(12) United States Patent
Ochiai

(10) Patent No.: US 6,640,821 B2
(45) Date of Patent: Nov. 4, 2003

(54) ENDOSCOPE CLEANING APPARATUS

(75) Inventor: Shoichi Ochiai, 7-66-111, Hishinumakaigan, Chigasaki-shi, Kanagawa (JP)

(73) Assignees: Shoichi Ochiai, Chigasaki (JP); Seiichi Moriyama, Tokyo (JP)

( * ) Notice: Subject to any disclaimer, the term of this patent is extended or adjusted under 35 U.S.C. 154(b) by 209 days.

(21) Appl. No.: 09/916,592

(22) Filed: Jul. 30, 2001

(65) Prior Publication Data

US 2002/0017316 A1 Feb. 14, 2002

(30) Foreign Application Priority Data

Aug. 7, 2000 (JP) ........................................ 2000-238181

(51) Int. Cl.[7] ................................................ B08B 3/12
(52) U.S. Cl. ................ 134/102.1; 134/111; 134/169 R; 134/184; 422/300
(58) Field of Search ............................ 134/99.1, 102.1, 134/117, 169 R, 184; 422/300

(56) References Cited

U.S. PATENT DOCUMENTS 4,299,244 A * 11/1981 Hirai ...................... 134/102.1
5,405,587 A * 4/1995 Fernandez et al. .......... 422/292
6,361,751 B1 * 3/2002 Hight, III ................... 422/292
6,494,222 B1 * 12/2002 Mitsumori et al. ......... 134/184
2001/0042561 A1 * 11/2001 Kaketani et al. ........ 134/169 R

FOREIGN PATENT DOCUMENTS

| JP | 11-019025 | 1/1999 |
| JP | 11-226092 | 8/1999 |

* cited by examiner

Primary Examiner—Randy Golakowski
Assistant Examiner—Joseph L Perrin
(74) Attorney, Agent, or Firm—Oblon, Spivak, McClelland, Maier & Neustadt, P.C.

(57) ABSTRACT

A cleaning tube into which an endoscope is inserted for cleaning is formed with a flexible tube and curled like a loop. A bypass channel is used to link a first end of the cleaning tube and a second end thereof. A cleaning solution present in the cleaning tube is forcibly refluxed from one end of the cleaning tube to the other end over the bypass channel, whereby a circulation of the cleaning solution is produced in the cleaning tube. The endoscope is cleaned with the circulation.

16 Claims, 6 Drawing Sheets

ENDOSCOPE CLEANING APPARATUS

FIELD OF THE INVENTION

The present invention relates to an apparatus for cleaning an endoscope that is inserted into a living body in order to diagnose or cure an organ or collect a sample after the endoscope is used.

RELATED ART

FIG. 7 shows an example of an endoscope. An endoscope 1 has an insertion member 2, a hand-held operator unit 3, a universal cord 4, and a connector unit 5. The insertion member 2 is flexible and elongated, and inserted into a living body. The hand-held operator unit 3 is fixed to the proximal end of the insertion member 2. The universal cord 4 extends from the hand-held operator unit 3. The connector unit 5 is fixed to an end of the universal cord 4. An illumination window and an observation window or a suction port and an aeration/perfusion port are formed in the distal part of the insertion member 2. The windows or ports open on conductors or passage holes that run through the insertion member 2 and universal cord 4 and that are led the hand-held operator unit 3 and connector unit 5. The passage holes meet the holes of a suction button 6 and an aeration/perfusion button 7 or the holes of a suction base 8 and an aeration/perfusion channel connector 9. After the insertion member 2 is inserted into a living body, while the hand-held operator unit 3 is used to perform required manipulations, an organ is diagnosed or cured, or a sample is collected.

This sort of endoscope is used in common among a plurality of patients. After the endoscope is used, the endoscope must be fully cleaned and disinfected in order to prevent 100% infection of bacteria through the endoscope. Therefore, various cleaning means for cleaning endoscopes have been proposed in the past.

For example, Japanese Unexamined Patent Publication No. 11-226092 has disclosed an apparatus for cleaning an endoscope while circulating a cleaning solution stored in a cleaning vessel in which the elongated endoscope is stowed while being rounded. However, this method of cleaning an endoscope while immersing it in a cleaning solution kept in the capacious cleaning vessel needs a large amount of cleaning solution and requires high running costs. Besides, efficiency in cleaning is poor and cleaning requires much time. Moreover, a large space is needed for cleaning.

Japanese Unexamined Patent Publication No. 11-19025 has disclosed a cleaning apparatus for cleaning an endoscope that is bent to be fitted in a groove which is curled to have several turns and into which a cleaning solution is poured. Herein, the groove is formed in the upper surface of the top plate of the apparatus while being slightly inclined. According to the method implemented in the apparatus, compared with the aforesaid method, an endoscope can be cleaned with a small amount of cleaning solution. However, since an endoscope is merely brought into contact with a cleaning solution that flows through the groove in the direction of inclination, the endoscope cannot be cleaned reliably and fully. Cleaning efficiency is poor. Besides, since the groove curled to have several turns is formed in the upper surface of the top plate of the cleaning apparatus, a large planar space is needed. This results in the bulky cleaning apparatus. Moreover, in order to fit an endoscope in the center of the groove shaped to make several turns, the endoscope must be bent to exhibit a small radius of curvature. Unnatural force is therefore likely to be imposed on the endoscope.

DISCLOSURE OF THE INVENTION

Accordingly, an object of the present invention is to provide a cleaning technology that is economic and superior in cleaning efficiency and that reliably cleans an elongated endoscope in a limited cleaning space with a limited amount of cleaning solution.

In order to accomplishing the above object, according to the present invention, there is provided an endoscope cleaning apparatus consisting mainly of a casing, a cleaning tube, a cleaning solution feeding mechanism, a bypass channel, a circulation pump, and a discharge pump. The casing has an insertion port pipe that opens on the top thereof, and a discharge port pipe that is located on the bottom thereof. An endoscope is inserted through the insertion port pipe, and the discharge port pipe can be opened or closed using a valve. The cleaning tube is a flexible tube curled like a loop, and placed substantially lengthwise in the casing. A first end of the cleaning tube is joined to the endoscope insertion port pipe, and the other second end thereof is joined to the discharge port pipe. The cleaning solution feeding mechanism feeds a cleaning solution to the cleaning tube. The bypass channel links the first end of the cleaning tube and the second end thereof. The circulation pump forces the cleaning solution present in the cleaning tube to reflux from one end of the cleaning tube to the other end thereof over the bypass channel, whereby a flow of the cleaning solution is produced in the cleaning tube. The discharge pump discharges the cleaning solution present in the cleaning tube through the discharge port pipe.

In the cleaning apparatus in accordance with the present invention having the foregoing components, the insertion member of an endoscope that is inserted into a living body is inserted into the cleaning tube through the insertion port pipe while being bent to trace a loop. A cleaning solution is poured into the cleaning tube, and then forcibly refluxed from one end of the cleaning tube to the other end thereof over the bypass channel. Consequently, a flow of the cleaning solution is produced in the cleaning tube. The flow is used to clean the endoscope. At this time, the speed of the circulating cleaning solution is high and the cleaning solution is agitated to be turbulent. The endoscope that comes into contact with the cleaning solution is therefore reliably and perfectly cleaned with the cleaning solution. Moreover, the use of the cleaning tube curled like a loop makes it possible to reliably clean the elongated endoscope within a limited cleaning space with a limited amount of cleaning solution. This is very economic and superior in cleaning efficiency.

According to the present invention, preferably, a direction in which the cleaning solve is refluxed using the bypass channel and circulation pump is able to be changed from a forward direction to a reverse direction or vice versa.

According to the present invention, preferably, a bubble generating means for supplying bubbles into the cleaning solution present in the cleaning tube is connected to the cleaning tube and located near the second end of the cleaning tube. Moreover, a vibrator for vibrating the cleaning tube may be connected to the cleaning tube and located near a middle point of the cleaning tube. Furthermore, an ultrasonic device for irradiating ultrasonic waves to the cleaning solution may be fixed to the cleaning tube in combination with or in place of the vibrator.

Preferably, according to the present invention, the crossing portions of the cleaning tube curled like a loop, which lie on the bottom of the casing, are linked to communicate with each other by a small-diameter passage.

Concretely, according to the present invention, the cleaning tube has a solution feed port pipe, through which a cleaning solution is fed, located at the second end thereof. The cleaning solution feeding mechanism is connected to the solution feed port. The cleaning solution feeding mechanism can selectively feed tap water, and an alkaline solution and an acidic solution that result from electrolysis of brine.

Preferably, the cleaning apparatus in accordance with the present invention has an internal hole cleaning means that circulates the cleaning solution present in the cleaning tube through passage holes formed in an endoscope by performing suction or injection so as to clean the passage holes.

DESCRIPTION

Figure 1:
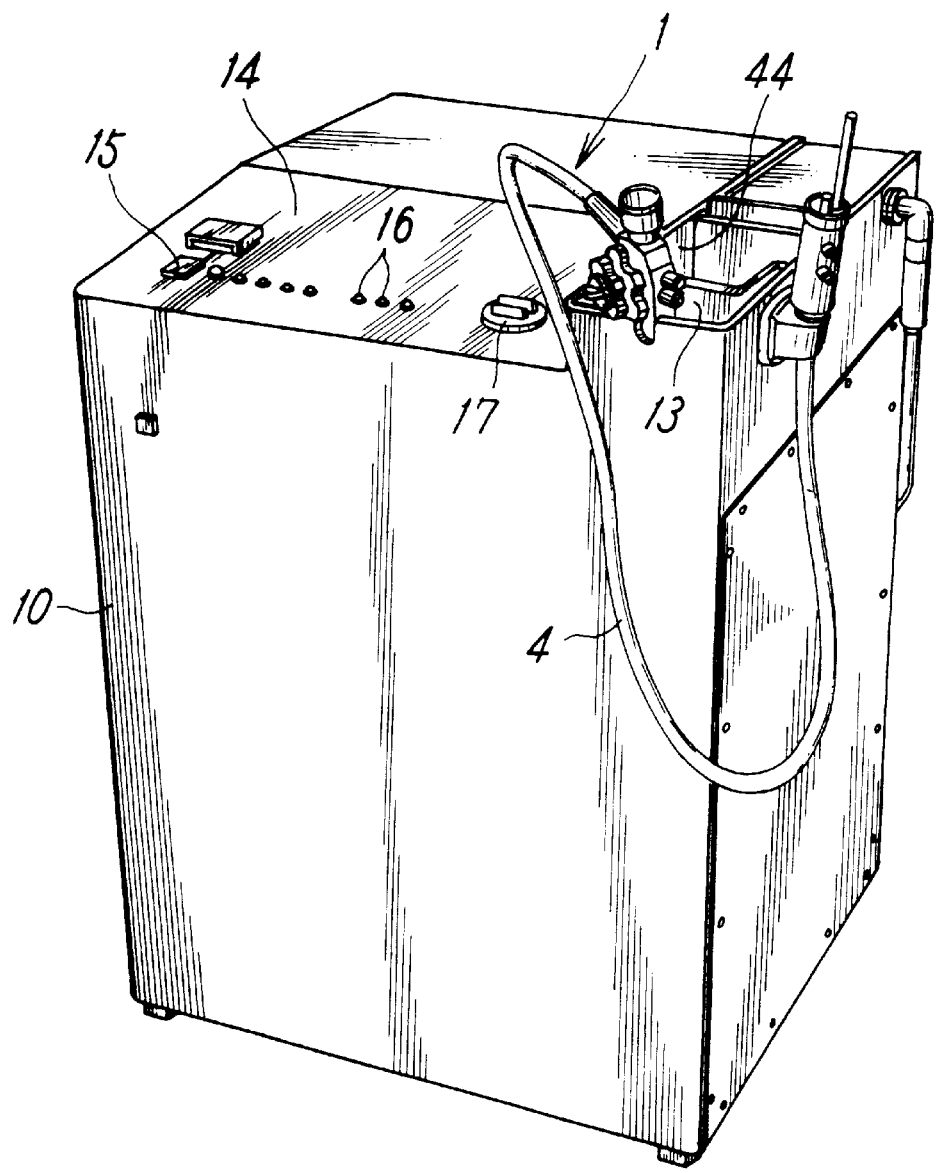
FIG. 1 is a perspective view showing an embodiment of an endoscope cleaning apparatus in accordance with the present invention.
Figure 2:
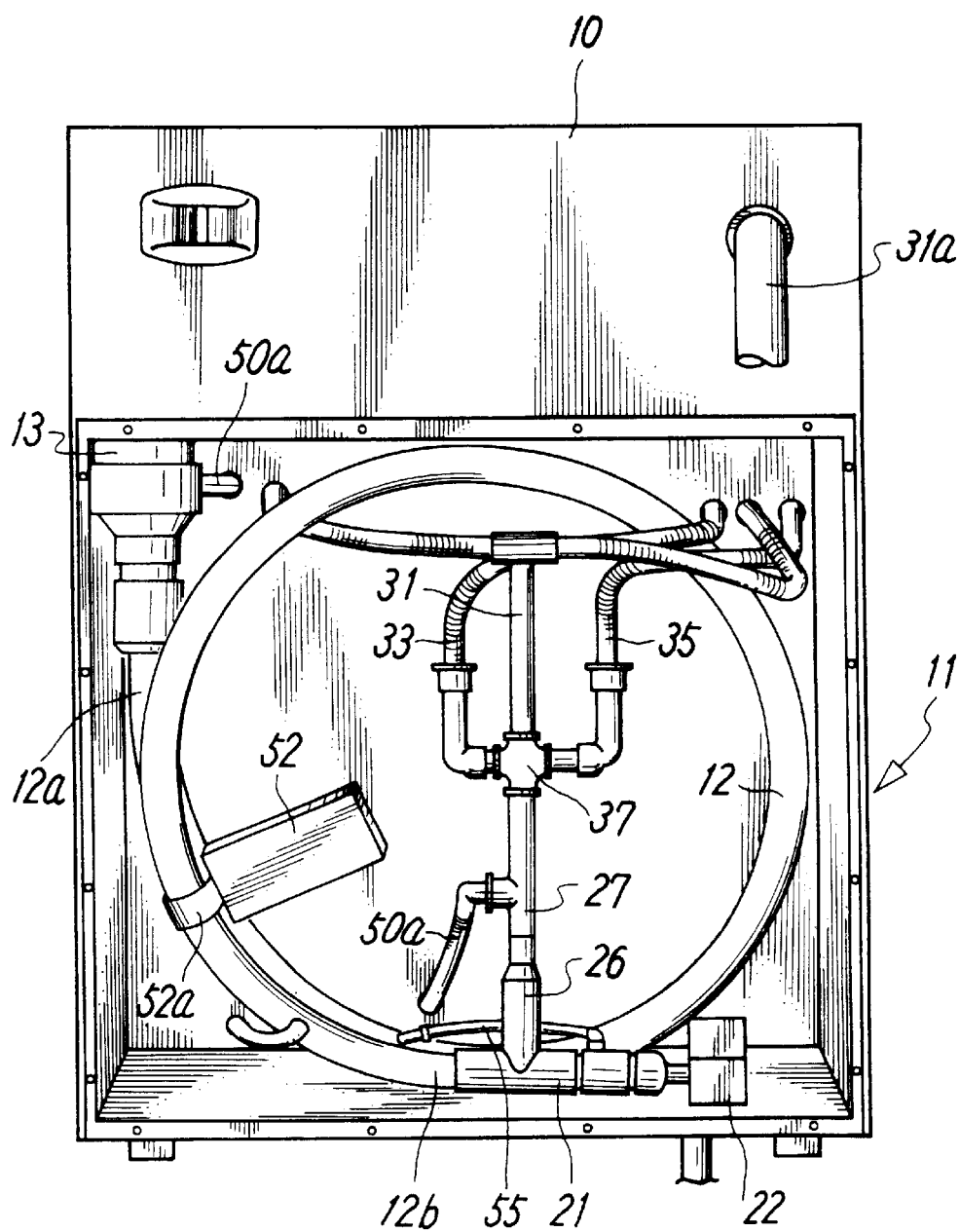
FIG. 2 is a side view showing the cleaning apparatus shown in FIG. 1 with a side cover detached.

FIG. 1 and FIG. 2 show a preferred embodiment of a cleaning apparatus in accordance with the present invention. In the drawings, there is shown a casing 10 shaped like a box. The casing 10 accommodates a cleaning mechanism 11 that cleans an endoscope 1 shown in FIG. 5. An insertion port pipe 13 that looks like a hollow opens on the top of the casing 10 near the side edge of the top thereof. The endoscope 1 is inserted into a cleaning tube 12 included in the cleaning mechanism 11 through the insertion port pipe 13. A panel 14 serving as an operator panel and a display panel is formed to face a user. Operation switches 15 and indicator lamps 16 are exposed on the panel 14.

Figure 3:
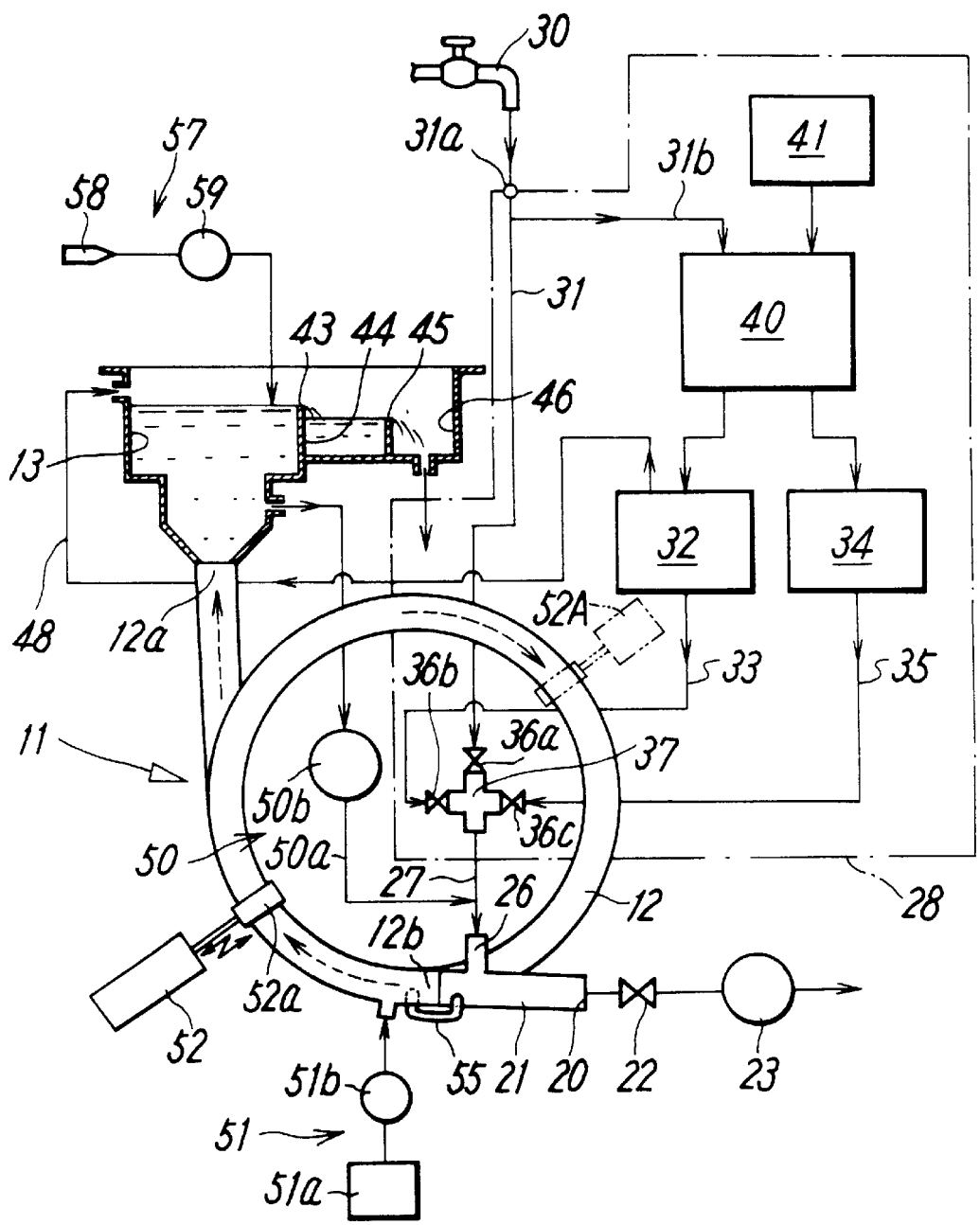
FIG. 3 shows the overall configuration of a cleaning apparatus in accordance with the present invention.
Figure 4:
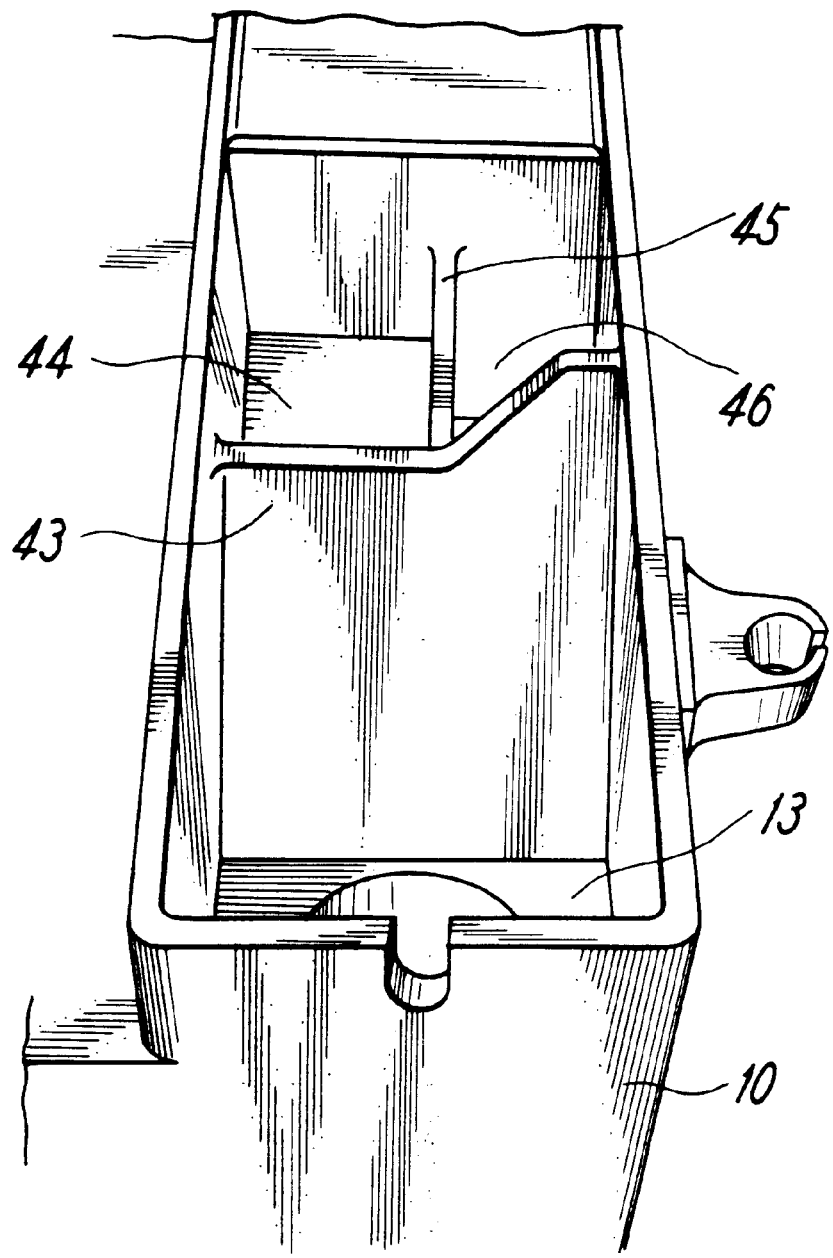
FIG. 4 is a perspective view showing in enlargement part of the top of the cleaning apparatus shown in FIG. 1.

The cleaning mechanism 11 has the cleaning tube 12 included for cleaning an insertion member 2 of the endoscope that is inserted into a living body. The cleaning mechanism 11 has members thereof arranged as shown in FIG. 3. The cleaning tube 12 is a flexible tube that is made of a synthetic resin and that is curled like a loop. As seen from FIG. 2, the cleaning tube curled like a loop is placed lengthwise near the endoscope insertion port pipe 13 in the casing 10. A first end 12a of the cleaning tube 12 is joined to the endoscope insertion port pipe 13, and an opposite end or a second end 12b thereof is joined to a discharge port pipe 20, which is located on the bottom of the casing 10, with a joint 21 between them. A discharge pump 23 is connected to the discharge port pipe 20 with a valve 22 between them. The first end 12a is located high above the bottom of the casing, while the second end 12b is located low. Moreover, the cleaning tube 12 has the first end 12a and second end 12b thereof, which are joined to the insertion port pipe 12 and discharge port pipe 20, substantially secured to the casing 10. The intermediate portion of the cleaning tube curled like a loop is not fixed to the casing 10 but can vibrate freely.

As mentioned above, the cleaning tube 12 is curled like a loop and placed lengthwise. Therefore, the cleaning tube 12 can be placed neatly in a limited planar space. This is quite helpful in making efforts to design the cleaning apparatus compactly. According to the present invention, when it says that the cleaning tube is placed "lengthwise," it by no means signifies that the cleaning tube is placed perfectly vertically. The cleaning tube may be tilted. For example, as long as the tilt angle is about 45° or less, the object of the present invention can be accomplished satisfactorily.

A cleaning solution feed port pipe 26 is branched out from the joint 21 and located near the second end 12b of the cleaning tube 12. A cleaning solution feeding mechanism 28 is connected to the solution feed port pipe 26 over a solution feed tube 27. The cleaning solution feeding mechanism 28 selectively feeds tap water, an alkaline solution, and an acidic solution as a cleaning solution. The cleaning solution feeding mechanism 28 further includes a tap water pipe 31, an alkaline solution pipe 33, an acidic solution pipe 35, and a pipe joint 37. The tap water pipe 31 has a connection port 31a that meets the hole of a water tap 30. The alkaline solution pipe 33 is led to a first tank 32 in which an alkaline solution is stored. The acidic solution pipe 35 is led to a second tank 34 in which an acidic solution is stored. These pipes are joined to the pipe joint 37 via valves 36a, 36b, and 36c. The pipe joint 37 is joined to the solution feed tube 27. By opening or closing any of the valves 36a, 36b, and 36c, any of the cleaning solutions flows out through the solution feed tube 27 located near the second end 12b of the cleaning tube 12. The cleaning solution is thus poured into the cleaning tube 12 until it overflows through the endoscope insertion port pipe 13 located near the first end 12a.

An electrolytic solution generator 40 for generating an alkaline solution and an acidic solution by electrolyzing brine is connected to each of the first tank 32 and second tank 34. The electrolytic solution generator 40 mixes tap water fed over a branch pipe 31b branching out from the tap water pipe 31 with brine fed through an injection port 17 formed in the top of the casing 10, and then electrolyzes the mixture. Consequently, a strong acidic solution is generated on an anode and a strong alkaline solution is generated on a cathode. The alkaline solution is stored in the first tank 32 that is sealed, and the acidic solution is stored in the second tank 34 that is sealed. Incidentally, the principles of electrolysis implemented in the electrolytic solution generator 40 are already known. A further description will therefore be omitted.

An auxiliary chamber 44 adjoins the electrode insertion port pipe 13, which opens on the top of the casing 10, with a first partition 43 between them. The first partition 43 is higher than a perimetric wall. A discharge chamber 46 adjoins the auxiliary chamber 44 with a second partition 45, which is higher than the first partition 43, between them. Components of the endoscope 1 disassembled for cleaning of the endoscope 1 and accessories thereof are stowed in the auxiliary chamber 44, and then cleaned. The components include, for example, the aeration/perfusion button 7 detached from an aeration/perfusion cylinder 7a, the suction button 6 detached from a suction cylinder 6a, and caps. When a cleaning solution is poured into the cleaning tube 12 for the purpose of cleaning the endoscope 1, part of the cleaning solution overflows the endoscope insertion port pipe 13 and first partition 43, and flows into the auxiliary chamber 44. After cleaning the components and accessories stowed in the auxiliary chamber 22, the cleaning solution overflows the second partition 45 and flows into the discharge chamber 46. The cleaning solution is then discharged to outside through a discharge port formed in the bottom of the discharge chamber.

A discharge tube 48 extending from the first tank 32 in which an alkaline solution is stored is joined to the endoscope insertion port pipe 13. Chlorine generated together with an alkaline solution during electrolysis flows into the first tank 32. The chlorine is discharged to the endoscope insertion port pipe 13 over the discharge tube 48. The chlorine discharged to the insertion port pipe 13 overflows, similarly to the cleaning solution, the first partition 43 and flows into the auxiliary chamber 44. The chlorine then overflows the second partition 45 and flows into the discharge chamber 46. The chlorine is then discharged to output through the discharge hole.

Moreover, a bypass channel 50 linking the first end 12a and second end 12b is joined to the cleaning tube 12. The bypass channel 50 includes an external pipe 50a that links the endoscope insertion port pipe 13 and solution feed port pipe 26, and a pump 50b incorporated in the pipe 50a. When the endoscope 1 is cleaned, the cleaning solution present in the endoscope insertion port pipe 13 is forcibly refluxed to the second end 12b over the bypass channel 50. This results in a high-speed circulation of the cleaning solution oriented from the second end 12b to the endoscope insertion port pipe 13.

A bubble generating means 51 for supplying bubbles into the cleaning solution for the purpose of improving cleaning efficiency and a vibrator 52 for vibrating the cleaning tube 12 are joined to the cleaning tube 12.

The bubble generating means 51 consists of an air feeder 51a that feeds air, and a pump 51b that supplies the air fed from the air feeder 51a into the cleaning tube 12.

The bubble generating means 51 is connected to the cleaning tube 12 near the second end 12b of the cleaning tube 12. Bubbles are supplied into the cleaning solution that circulates through the cleaning tube at a high speed, whereby agitation of the cleaning solution is facilitated. Consequently, cleaning efficiency is improved.

The vibrator 52 is mounted on the casing 10. A vibration propagating member 52a included in the vibrator 52 is coupled to one of the crossing portions of the cleaning tube 12 that is curled like a loop. The vibrator 52 thus vibrates the cleaning tube 12 at, for example, 140 cycles per min. Since the vibrator 52 vibrates the cleaning tube 12, the endoscope 1 shifts inside the cleaning tube 12 relative to the cleaning tube 12. Consequently, the endoscope 1 comes into contact with the cleaning solution without fail. Besides, since the portion of the endoscope 1 being in contact with the inner wall of the cleaning tube 12 is separated from the inner wall thereof and brought into contact with the cleaning solution. This resolves such a drawback that a portion of the endoscope 1 is held in contact with the cleaning tube 12 and is not cleaned. The outer surface of the endoscope 1 is entirely cleaned without fail. In addition to the vibrator 52, another vibrator 52A analogous to the vibrator 52 may be coupled to the cleaning tube as indicated with a chain line in FIG. 3.

Moreover, the crossing portions of the cleaning tube 12 that lie on the bottom of the casing are linked to communicate with each other by a small-diameter passage 55. In other words, the crossing portions of the cleaning tube 12 curled like a loop, which lie on the bottom of the casing, are bypassed by the passage 55. This prevents occurrence of such an incident that after cleaning is completed, when the cleaning solution present in the cleaning tube 12 is discharged through the discharge port pipe 20 using the pump 23, part of the cleaning solution is not sucked but remains in the lower half of the insertion tube curled like a loop. Incidentally, the cross-sectional area of the passage 55 is set to such a value that the passage 55 will not hinder production of the circulation of the cleaning solution inside the cleaning tube 12.

The cleaning apparatus further includes one or two inner hole cleaning means 57 that clean inner holes such as a suction hole and a perfusion hole formed inside the endoscope 1. The inner hole cleaning means 57 consists of a tube 58, a cleaning pump 59, and a drying pump 60. The tube 58 is joined to the suction base 8 or aeration/perfusion connector 9 that opens on the connector unit 5 distal to the universal cord 4 of the endoscope 1. The cleaning pump 59 and drying pump 60 are connected to the tube 58 so that they can be switched using a switching valve 61. The distal end of the tube 58 opens on the inside of the endoscope insertion port pipe 13 that opens on the top of the casing 10.

The tube 58 is joined to the suction base 8 or aeration/perfusion connector 9. For cleaning, the cleaning pump 59 is used to suck a cleaning solution present in the cleaning tube 12 into the suction hole or perfusion hole through the suction port or perfusion port that opens on the distal end of the insertion member 2 of the endoscope 1. With the sucked cleaning solution, the inside of the suction hole or perfusion hole is cleaned. Alternatively, the cleaning solution may be injected into the suction hole or perfusion hole through the suction base 8 or aeration/perfusion connector 9 to which the tube 58 is joined, whereby the inside of the suction hole or perfusion hole may be cleaned.

Moreover, after cleaning is completed, the state of the switching valve 61 is changed in order to use the drying pump 60. The cleaning solution remaining in the suction hole or perfusion hole is discharged and dried by supplying compressed air or by sucking the cleaning solution.

Next, an example of a method for cleaning the endoscope 1 using the cleaning apparatus that has the foregoing components will be described below.

First, the insertion member 2 of the endoscope 1 is inserted into the cleaning tube 12, which is curled like a loop, through the endoscope insertion port pipe 13 that opens on the top of the casing 10. At this time, the insertion member 2 is bent to trace a loop. Although the insertion member 2 is elongated, since the cleaning tube 12 is curled like a loop, the insertion member 2 can be reliably stowed in the cleaning tube 12 as a whole.

Next, an enzymatic cleaner is injected through the injection port 17 formed in the top of the casing 10 and poured into the cleaning tube 12 by way of the endoscope insertion port pipe 13. Tap water is fed to the cleaning tube 12 through the solution feed port pipe 26 via the valve 36a over the tap water pipe 31. After the cleaning tube 12 is filled with tap water, the endoscope insertion port pipe 13 is also filled therewith. Tap water is further kept fed until part of the tap water overflows the first partition 43 and flows into the auxiliary chamber 44, and then overflows the second partition 45 and flows out through the discharge port.

When feeding tap water that has the enzymatic cleaner mixed therein is completed, the valve 36a is closed. The pump 50b incorporated in the bypass channel 50 is activated, and the bubble generating means 51 and vibrator 52 are activated, too. A first cleaning step is then performed using tap water with the enzymatic cleaner mixed therein. At this time, in the cleaning tube 12, the cleaning solution is forcibly refluxed from the first end 12a to the second end 12b over the bypass channel 50. This brings about a high-speed circulation oriented from the second end 12b to the first end 12a. The endoscope 1 brought into contact with the circulation has slime and a gelled material, which have adhered to the surface of the endoscope 1, washed away.

Moreover, when the bubble generating means 51 supplies bubbles into the cleaning solution, agitation of the cleaning solution is facilitated. This results in improved cleaning efficiency.

Furthermore, when the vibrator 52 vibrates the cleaning tube 12, the endoscope 1 lying through the cleaning tube 12 shifts relative to the cleaning tube 12 or vibrates to come into contact with the cleaning solution without fail. Besides, the portion of the endoscope in contact with the inner wall of the cleaning tube 12 is separated from the cleaning tube 12 and brought into contact with the cleaning solution. The drawback that a portion of the endoscope 1 is held in contact with the cleaning tube 12 and not cleaned is resolved. The outer surface of the endoscope 1 is entirely cleaned without fail.

While the outer surface of the endoscope is being cleaned, the suction hole and perfusion hole formed inside the endoscope are also cleaned owing to the inner hole cleaning means 57. At this time, the cleaning pump 59 is made usable by changing the state of the switching valve 61. Consequently, the cleaning solution present in the cleaning tube 12 is sucked into the suction hole or perfusion hole through the suction port or aeration/perfusion port that opens on the distal end of the insertion member 2 of the endoscope 1. The inside of the suction hole or perfusion hole is thus cleaned.

When the first cleaning step using tap water that has the enzymatic cleaner mixed therein is completed, the valve 22 is opened and the pump 23 is activated. The cleaning solution present in the cleaning tube 12 is forcibly discharged while being sucked through the discharge port pipe 20. Since the crossing portions of the cleaning tube 12 curled like a loop, which lie on the bottom of the casing, are bypassed by the small-diameter passage 55, the cleaning solution is entirely discharged. An incident that part of the cleaning solution is not sucked but remains in the lower half of the insertion tube curled like a loop will not take place.

When discharge of the cleaning solution is completed, a second cleaning step is performed using a strong alkaline solution. Specifically, the alkaline solution stored in the first tank 32 is fed to the cleaning tube 12 over the alkaline solution pipe 33 by opening the valve 36b. Thereafter, the pump 50b in the bypass channel 50 is activated, and the bubble generating means 51 and vibrator 52 are activated, too. Cleaning using the alkaline solution is then carried out in the same manner as the cleaning using tap water that has the enzymatic cleaner mixed therein is. At the second cleaning step, fat, blood, protein, or the like adhering to the endoscope 1 are dissolved and removed.

Even in this case, the suction hole or perfusion hole formed inside the endoscope 1 is cleaned owing to the inner hole cleaning means 57.

When the second cleaning step using an alkaline solution is completed, a third cleaning step is performed using a strong acidic solution. Specifically, the acidic solution stored in the second tank 34 is fed to the cleaning tube 12 over the acidic solution pipe 35 by opening the valve 36c. Thereafter, the pump 50b in the bypass channel 50 is activated, and the bubble generating means 51 and vibrator 52 are activated, too. At the third cleaning step using the acidic solution, the endoscope 1 is cleaned and sterilized.

Even in this case, the suction hole or perfusion hole formed inside the endoscope 1 is sterilized and cleaned owing to the inner hole cleaning means 57.

When the third cleaning step using the acidic solution is completed, a fourth cleaning step is performed using tap water again. Specifically, tap water is fed to the cleaning tube 12 over the tap water pipe 31 by opening the valve 36a. Thereafter, the pump 50b in the bypass channel 50 is activated, and the bubble generating means 51 and vibrator 52 are activated, too. Cleaning using tap water is carried out for rinsing in the same manner as the cleaning using the acidic solution is. At the fourth cleaning step using tap water, the acidic solution adhering to the endoscope 1 is washed away. Deterioration of the endoscope 1 derived from an acid can be prevented, and post-processing of the endoscope 1 can be simplified.

Even in this case, the suction hole or perfusion hole formed inside the endoscope 1 is rinsed owing to the inner hole cleaning means 57.

When all the cleaning steps are completed, the state of the switching valve 61 included in the inner hole cleaning means 57 is changed in order to use the drying pump 60. The cleaning solution remaining in the suction hole or perfusion hole is removed by supplying compressed air or by sucking the cleaning solution. Consequently, the inside of the suction hole or perfusion hole is dried up.

The thus cleaned endoscope 1 is taken out of the cleaning tube 12. The endoscope 1 has the outer surface thereof dried up, and is subjected to other required post-processing.

According to the present embodiment, the bypass channel 50 and pump 50b are used to reflux the cleaning solution present in the endoscope insertion port pipe 13 to the second end 12b. Consequently, a flow of the cleaning solution oriented from the second end 12b to the endoscope insertion port pipe 13 is produced in the cleaning tube 12. The reflux of the cleaning solution may be oriented in a direction opposite to the direction of the flow. Otherwise, the direction of the reflux may be changed from a forward direction to a reverse direction or vice versa. The flow of the cleaning solution may be reversed during cleaning.

Figure 5:
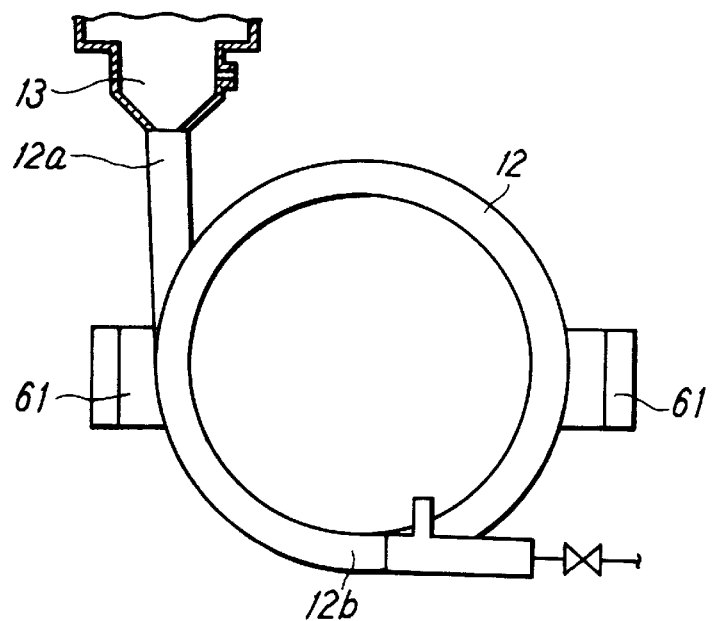
FIG. 5 is a plan view showing a major portion of another embodiment of an endoscope cleaning apparatus.

FIG. 5 shows a major portion of another embodiment of the cleaning apparatus. In this embodiment, an ultrasonic device 61 is fixed to the cleaning tube 12. The ultrasonic device 61 irradiates ultrasonic waves to a cleaning solution present in the cleaning tube 12 during cleaning. One or more ultrasonic devices 61 are fixed to the cleaning tube 12. The ultrasonic device 61 may be replaced with the vibrator 52 or may be used in combination with the vibrator 52. The other components are substantially identical to those of the aforesaid embodiment.

Figure 6:
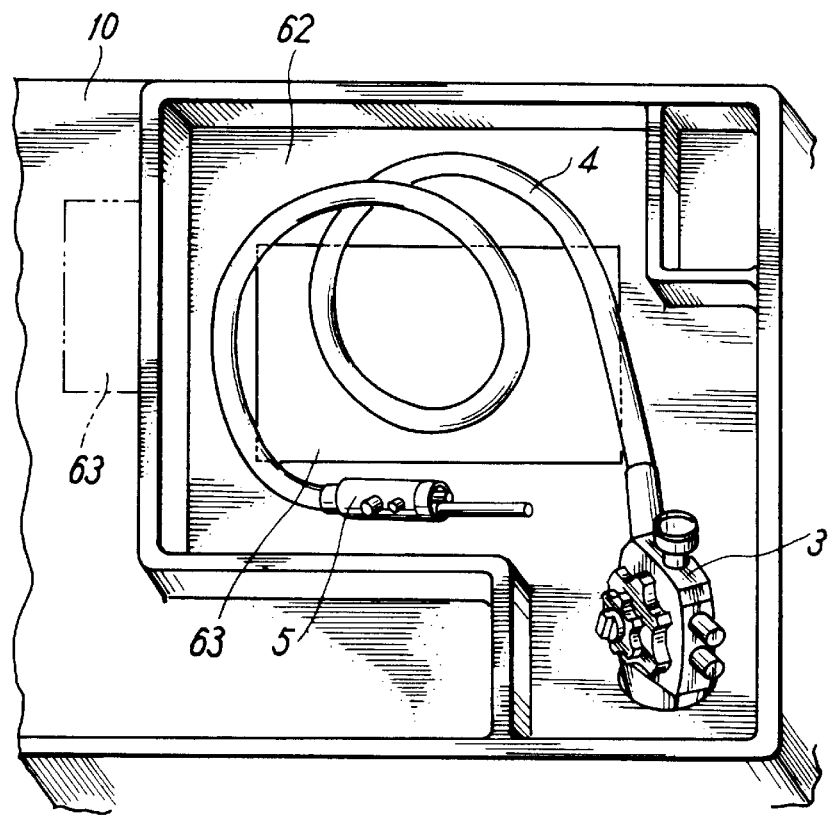
FIG. 6 is a plan view showing a major portion of still another embodiment of the endoscope cleaning apparatus.
Figure 7:
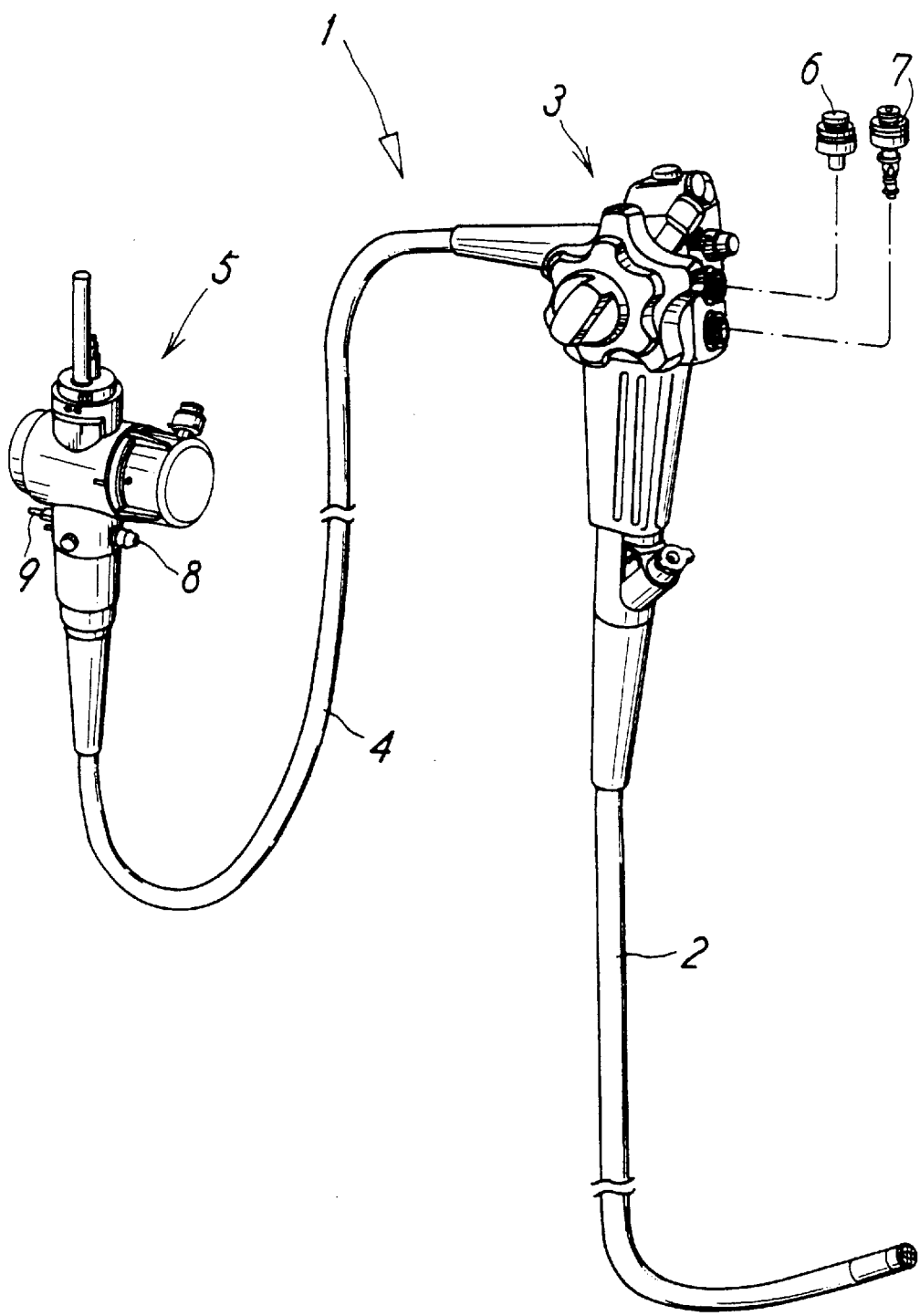
FIG. 7 is a perspective view showing an example of an endoscope.

FIG. 6 shows a major portion of still another embodiment of the cleaning apparatus. According to this embodiment, a cleaning vessel 62 is formed in the top of the casing 10. The hand-held operator unit 3 and universal cord 4 of the endoscope 1 as well as the connector unit 5 fixed to the end of the universal cord 4 are immersed in the cleaning vessel 62 for the purpose of cleaning. An ultrasonic device 63 is fixed to the bottom of the cleaning vessel 62, the side wall thereof, or any other proper place. The ultrasonic device 63 irradiates ultrasonic waves to a cleaning solution during cleaning. The other components are substantially identical to those of the aforesaid embodiments.

According to the present invention, an elongated endoscope can be cleaned reliably in a limited cleaning space with a limited amount of cleaning solution. The present invention is thus economic and superior in cleaning efficiency.

What is claimed is:

1. An endoscope cleaning apparatus comprising:
   a casing having an insertion port pipe, through which an endoscope is inserted and which opens on the top thereof, and a discharge port pipe that can be freely opened or closed using a valve and that is located on the bottom thereof;
   a cleaning tube that is a flexible tube curled like a loop, that is placed substantially lengthwise in said casing, that has a first end thereof joined to said endoscope insertion port pipe, and that has the other second end thereof joined to said discharge port pipe;
   a cleaning solution feeding mechanism for feeding a cleaning solution to said cleaning tube;
   a bypass channel linking said first end of said cleaning tube and said second end thereof;
   a circulation pump for forcibly refluxing a cleaning solution present in said cleaning tube from one end of said cleaning tube to the other end thereof over said bypass channel, and thus producing a flow of the cleaning solution in said cleaning tube; and
   a discharge pump for discharging a cleaning solution present in said cleaning tube through said discharge port pipe.

2. A cleaning apparatus according to claim 1, wherein said bypass channel and circulation pump are configured to reflux a cleaning solution from said first end of said cleaning tube to said second end thereof, whereby a flow of the cleaning solution oriented from said second end to said first end is produced in said cleaning tube.

3. A cleaning apparatus according to claim 1, wherein said circulation pump and bypass channel are designed so that the direction of the reflux of the cleaning solution over said bypass channel can be changed from a forward direction to a reverse direction or vice versa.

4. A cleaning apparatus according to claim 1, wherein said cleaning tube has a bubble generating means that supplies bubbles to a cleaning solution present in said cleaning tube.

5. A cleaning apparatus according to claim 1, wherein said cleaning tube has both ends thereof secured to said casing, and a vibrator is connected to an intermediate portion between said both ends and configured to vibrate said intermediate portion of said cleaning tube.

6. A cleaning apparatus according to claim 1, wherein said cleaning tube has an ultrasonic device that irradiates ultrasonic waves to a cleaning solution present in said cleaning tube.

7. A cleaning apparatus according to claim 1, wherein the crossing portions of said cleaning tube curled like a loop, which lie on the bottom of the casing, are linked to communicate with each other by a small-diameter passage.

8. A cleaning apparatus according to claim 1, wherein said cleaning tube has a solution feed port pipe, through which a cleaning solution is fed and which is located at said second end thereof, said cleaning solution feeding mechanism is connected to said solution feed port pipe, and said cleaning solution feeding mechanism selectively feeds tap water as well as an alkaline solution and an acidic solution that result from electrolysis of brine.

9. A cleaning apparatus according to claim 1, further comprising an inner hole cleaning means that circulates a cleaning solution present in said cleaning tube through passage holes formed inside an endoscope by performing suction or injection.

10. A cleaning apparatus according to claim 1, wherein a cleaning vessel used to clean components of an endoscope that are not inserted into said cleaning tube is formed in the top of said casing, and said cleaning vessel has an ultrasonic device that irradiates ultrasonic waves to a cleaning solution.

11. An endoscope cleaning apparatus comprising:
    a casing having an insertion port pipe, through which an endoscope is inserted and which opens on the top thereof, and a discharge port pipe that is freely opened or closed using a valve and that is located on the bottom thereof;
    a cleaning tube that is a flexible tube curled like a loop, that is placed substantially lengthwise in said casing, that has a first end thereof joined to said endoscope insertion port pipe, and that has the other second end thereof joined to said discharge port pipe;
    a solution feed port pipe located at said second end of said cleaning tube;
    a cleaning solution feeding mechanism that can selectively feed as a cleaning solution an alkaline solution and an acidic solution, which result from electrolysis of brine, and tap water, and feeds a selected cleaning solution to said cleaning tube through said solution feed port pipe;
    a bypass channel linking said first end of said cleaning tube and said second end thereof;
    a circulation pump for forcibly refluxing a cleaning solution present in said cleaning tube from said first end to said second end over said bypass channel, and thus producing a flow of the cleaning solution, which is oriented from said second end to said first end, in said cleaning tube;
    a bubble generating means for supplying bubbles to a cleaning solution present in said cleaning tube; and
    a discharge pump for discharging a cleaning solution present in said cleaning tube through said discharge port pipe.

12. A cleaning apparatus according to claim 11, wherein the crossing portions of said cleaning tube curled like a loop, which lie on the bottom of the casing, are linked to communicate with each other by a small-diameter passage.

13. A cleaning apparatus according to claim 11, wherein said cleaning tube has both ends thereof secured to said casing, and a vibrator is connected to an intermediate portion between said both ends and configured to vibrate said intermediate portion of said cleaning tube.

14. A cleaning apparatus according to claim 11, wherein an ultrasonic device for irradiating ultrasonic waves to a cleaning solution present in said cleaning tube is fixed to said cleaning tube.

15. A cleaning apparatus according to claim 11, further comprising an inner hole cleaning means that circulates a cleaning solution present in said cleaning tube through passage holes formed inside an endoscope by performing suction or injection, and thus cleans the passage holes.

16. A cleaning apparatus according to claim 11, wherein a cleaning vessel used to clean components of an endoscope that are not inserted into said cleaning tube is formed in the top of said casing, and said cleaning vessel has an ultrasonic device that irradiates ultrasonic waves to a cleaning solution.

* * * * *